(12) United States Patent
Sumita et al.

(10) Patent No.: US 6,268,119 B1
(45) Date of Patent: Jul. 31, 2001

(54) METHOD FOR SEPARATING CELLS

(75) Inventors: Masaya Sumita; Shuji Terashima, both of Oita (JP)

(73) Assignee: Asahi Medical Co., Ltd., Tokyo (JP)

( * ) Notice: Subject to any disclaimer, the term of this patent is extended or adjusted under 35 U.S.C. 154(b) by 0 days.

(21) Appl. No.: 09/341,879

(22) PCT Filed: Jan. 22, 1998

(86) PCT No.: PCT/JP98/00244

§ 371 Date: Jul. 19, 1999

§ 102(e) Date: Jul. 19, 1999

(87) PCT Pub. No.: WO98/32840

PCT Pub. Date: Jul. 30, 1998

(30) Foreign Application Priority Data

Jan. 24, 1997 (JP) .................................................. 9-024517
Feb. 24, 1997 (JP) .................................................. 9-054300
May 19, 1997 (JP) .................................................. 9-143002

(51) Int. Cl.$^7$ ............................. A01N 1/02; C12M 1/38; C12M 1/36; C12M 3/00; C12M 1/02
(52) U.S. Cl. ....................... 435/2; 435/286.5; 435/308.1; 435/261
(58) Field of Search .................. 435/2, 286.5, 308.1, 435/261; 210/600, 601, 602, 615, 616, 645, 649, 650, 651, 653, 654

(56) References Cited

U.S. PATENT DOCUMENTS

| Re. 35,267 | 6/1996 | Tsuru et al. . | |
|---|---|---|---|
| 4,255,267 | * 3/1981 | Hoehn et al. | 210/678 |
| 4,865,733 | * 9/1989 | Tsuru et al. | 210/266 |
| 5,085,781 | 2/1992 | Tsuru et al. . | |
| 5,780,281 | * 7/1998 | Yasukawa et al. | 435/176 |
| 5,795,483 | * 8/1998 | Ung-Chhun et al. | 201/645 |

FOREIGN PATENT DOCUMENTS

| 2175602 | * 12/1986 | (GB) . |
| 2 175 602 | 12/1986 | (GB) . |
| 54-119012 | 9/1979 | (JP) . |
| 64-5486 | 1/1989 | (JP) . |
| 2-200176 | 8/1990 | (JP) . |
| 8-69 | 3/1991 | (JP) . |
| 7-184991 | 7/1995 | (JP) . |
| 8-52206 | 2/1996 | (JP) . |
| 8-104643 | 4/1996 | (JP) . |
| 8-92001 | 4/1996 | (JP) . |
| WO 89/04168 | 5/1989 | (WO) . |
| WO 96/17514 | 6/1996 | (WO) . |

OTHER PUBLICATIONS

Sephadex LH–20 Catalog, 1973.*
BioRad Catalog, 1973.*
Fisher et al.; Cell Separation a Practical Approach, Oxford University Press pp. 191–212, 1998.*
Fisher Scientific Catalog pp. 579 (Glass Wool), 1988.*
Burdick & Jackson; Solvent Guide, 2nd Edition, p. 140, 1982.*
World Wide Web; http://www.axis–shield–poc.com/gradmed/cells/cells1.html, 2001.*
World Wide Web; http://www.axis–shield–poc.com/gradmed/cells/cells2.html, 2001.*
World Wide Web; http://www.nycomed–diagnostics.com/gradmed/gradient/grad4.html, 2001.*
Shi–Jia Gao, "'Xue Fu Zhu Yu Tang' Extract May Reduce the Red Cell Aggreability", Recent Advances in Cardiovascular Disease, vol. XVI. No. 1, Aug. 1995, pp. 124–127.
ABE, "Peripheral Blood Stem Cell Transplantation" NANKODO, pp. 172–175 and p. 425.

* cited by examiner

Primary Examiner—Jon P. Weber
Assistant Examiner—Patricia D Patten
(74) Attorney, Agent, or Firm—Young & Thompson

(57) ABSTRACT

A cell separation method comprising steps of introducing a cell-containing fluid containing cells to be recovered and cells to be removed, into a cell-capturing means capable of substantially capturing the cells to be recovered and substantially permitting passage therethrough of cells to be removed; taking out the resulting fluid containing the cells to be removed, from the cell-capturing means; and then introducing a liquid with a viscosity of not more than 500 mPa·s and not less than 5 mPa·s into the cell-capturing means to recover therefrom the cells to be recovered which have been captured by the cell-capturing means.

26 Claims, 3 Drawing Sheets

METHOD FOR SEPARATING CELLS

TECHNICAL FIELD

This invention relates to a method for separating and recovering only necessary cells from a fluid containing a mixture of various cells. The cells thus obtained can be used in providing therapy for various diseases, such as hematopoietic stem cell transplantation, and in fundamental sciences such as immunology and cell biology.

BACKGROUND ART

Japanese patent JP-A-54-119012 discloses a technique for recovering lymphocytes by capturing leukocytes on a filter from a body fluid such as blood containing leukocytes (granulocytes, monocytes and lymphocytes) and erythrocytes.

In the case of hematopoietic stem cell transplantation, cord blood stem cells are noted as a source of hematopoietic stem cells which does not cause any invasion to donors, and their clinical application is vigorously attempted, mainly in countries in Europe and America. Since cord blood stem cells are rarely transplanted to a patient immediately after being collected from a donor, unlike in other hematopoietic stem cell transfers, i.e., bone marrow transplantation and peripheral blood stem cell transplantation, they should be preserved for use after the collection. Such preservation is often needed, particularly in the case of unrelated setting. Before cryopreservation of cord blood, the separation of nucleated cells and the removal of erythrocytes is considered necessary in order to prevent side effects of erythrocytes lysis after thawing, and to reduce the volume during the cryopreservation. At present, cord blood is preserved after the separation, in most cases ("Peripheral Blood Stem Cell Transplantation" p. 173, NANKODO Ltd.). JP-B-8-69 discloses details of a protocol for separating cord blood by a Ficoll-Hypaque method, a centrifugation method using a liquid having an adjusted specific gravity, hereinafter referred to as "Ficoll method". The Ficoll method, however, is disadvantageous in that it is only feasible on a laboratory level and requires very troublesome and time-consuming operations. International Publication No. WO 96/17514 discloses a bag system and method for separating erythrocytes in cord blood by agglutination and precipitation by the use of hydroxyethyl starch to obtain a concentrated nucleated cell suspension, and a cell suspension obtained by that method. This method is somewhat superior to the Ficoll method, a conventional method in that it involves fewer troublesome operations, but it also is time-consuming because two centrifugation runs are necesary.

On the other hand, some methods for separating hematopoietic stem cells have been reported as substitutes for the Ficoll method and the erythrocyte aggutination and removal. JP-A-8-104643 discloses a method for recovering hematopoietic stem cells by capturing them on a filter permeable to erythrocytes, and then causing a liquid flow in a direction opposite to the first liquid flow direction. This method, however, merely uses Hanks' Balanced Salt Solution (HBSS) as the liquid for the recovery.

Dextran is a polysaccharide composed of glucose units as monomer units mainly by $\alpha$-1,6 linkages, and has been used since early times as an agent for separating leukocytes. The separation of leukocytes by the use of dextran, however, utilizes the effect of dextran as a hemagglutinating agent. After erythrocytes in a test tube are agglutinated and precipitated, centrifugation is carried out if necessary, and then leukocytes in the supernatant are recovered with a pipet (Shiro Miwa, Rinsho Kensa Gijutsu Zensho, Vol. 3, "Ketsueki Kensa" p. 425). Such an effect is not characteristic of only dextran, because hydroxyethyl starch and the like have the same hemagglutinating effect as that of dextran.

Next, systems for separating hematopoietic stem cells are described below. JP-A-7-184991 discloses an assembly for collecting cord blood, in particular, a filter for removing contaminants in cord blood, such as aggregates (e.g. microaggregates), tissue particles, one particles, steatomas, etc., which is provided before a container for blood collection. This filter, however, is not for capturing cells which should be recovered, but for removing contaminants. Even if a material capable of capturing hematopoietic stem cells is used in the filter by chance, this reference does not describe the recovery of the captured hematopoietic stem cells at all.

JP-A-8-52206 discloses an apparatus comprising a membrane type plasma separator, as an apparatus for collecting cord blood which is used for separating hematopoietic stem cells from cord blood collected. This reference also discloses another separation method using an apparatus for density gradient separation, i.e., separation by the Ficoll method.

The present invention is intended to provide a method for separating cells which are desired to be recovered (hereinafter referred to as "cells to be recovered" or "necessary cells") from a mixture of necessary cells and unnecessary cells (hereinafter referred to as "cells to be removed") by a simple and rapid procedure. This procedure comprises a cell separation method which captures necessary cells by use of a capturing means such as filtering a fluid containing the cell mixture, and then recovering the captured cells with high recovery. The present invention also provides a line system obtained by embodiment of this method for practical clinical employment. The present invention also provides a recovering liquid used in said system, and a cell-containing fluid obtained by using the method.

In order to solve the problems identified in the prior art, the present inventors noted properties of a liquid for recovering cells from a cell-capturing means, and earnestly investigated these properties to conclude that when cells are recovered by using a recovering liquid having a definite viscosity, a high recovery can be attained. As a result of earnest investigation on the compositions of various recovering liquids, the present inventors found such a striking effect that, when cells are recovered by using a physiological solution containing dextran, a very high recovery can be attained. Thus, the objectives of the present invention have been accomplished.

DISCLOSURE OF THE INVENTION

One aspect of the present invention is directed to a cell separation method comprising steps of introducing a cell-containing fluid containing cells to be recovered and cells to be removed into a cell-capturing means capable of substantially capturing the cells to be recovered and substantially permitting passage therethrough of the cells to be removed. Then, the resulting fluid containing the cells to be removed is taken from the cell-capturing means, and then a liquid with a viscosity of not more than 500 mPa·s and not less than 5 mPa·s is introduced into the cell-capturing means to recover therefrom the cells to be recovered which have been captured by the cell-capturing means.

Another aspect of the present invention is directed to a cell separation and preservation method comprising steps of introducing a cell-containing fluid containing cells to be recovered and cells to be removed, into a cell-capturing means capable of substantially capturing the cells to be recovered, and substantially permitting passage therethrough of the cells to be removed. The resulting fluid containing the cells to be removed is taken out of the cell-capturing means, and a liquid with a viscosity of not more than 500 mPa·s and not less than 5 mPa·s is introduced into the cell-capturing means to recover therefrom the cells to be recovered which have been captured by the cell-capturing means. The recovered cells are then preserved.

Another aspect of the present invention is directed to a cell separation and preservation method comprising steps of introducing a cell-containing fluid containing cells to be recovered and cells to be removed into a cell-capturing means capable of substantially capturing the cells to be recovered, and substantially permitting passage of the cells to be removed. The resulting fluid containing the cells to be removed is taken from the cell-capturing means, and a liquid with a viscosity of not more than 500 mPa·s and not less than 5 mPa·s is introduced into the cell-capturing means to recover therefrom the cells to be recovered which have been captured by the cell-capturing means. The recovered cells are then subjected to cryopreservation and thawing.

Still another aspect of the present invention is directed to a cell separation system comprising a cell-capturing means which is capable of substantially capturing cells to be recovered and substantially permitting passage therethrough of cells to be removed, which has at least an inlet and an outlet. A line for introducing into the cell-capturing means a cell-containing fluid containing the cells to be recovered and the cells to be removed is connected upstream to the inlet of the cell-capturing means. A line for introducing a liquid into the cell-capturing means is connected downstream to the outlet of the cell-capturing means, and a line for cell recovery from the inlet side of the cell-capturing means is connected upstream to the inlet of the cell-capturing means.

Still another aspect of the present invention is directed to a cell separation method comprising steps of introducing a cell-containing fluid containing cells to be recovered and cells to be removed into a cell-capturing means capable of substantially capturing the cells to be recovered and substantially permitting passage therethrough of the cells to be removed, through a line connected upstream to the inlet of the cell-capturing means. The resulting fluid containing the cells to be removed is taken out through the outlet of the cell-capturing means, and then a liquid with a viscosity of not more than 500 mPa·s and not less than 5 mPa·s is introduced into the cell-capturing means through a line connected downstream to the outlet of the cell-capturing means to recover the cells to be recovered which have been captured by the cell-capturing means, through a line connected upstream to the inlet of the cell-capturing means.

Still another aspect of the present invention is directed to a liquid containing hematopoietic stem cells which is substantially free from erythrocytes and/or platelets and has a viscosity of not more than 500 mPa·s and not less than 5 mPa·s Still another aspect of the present invention is directed to a liquid containing cells to be recovered and substantially having no cells to be removed which is obtained by a cell separation method comprising steps of introducing a cell-containing fluid containing cells to be recovered and cells to be removed into a cell-capturing means capable of substantially capturing the cells to be recovered and substantially permitting passage therethrough of the cells to be removed. The resulting fluid containing the cells to be removed is taken out from the cell-capturing means, and then a liquid with a viscosity of not more than 500 mPa·s and not less than 5 mPa·s is introduced into the cell-capturing means to recover therefrom the cells to be recovered which have been captured by the cell-capturing means.

Still another aspect of the present invention is directed to a liquid for recovering captured cells from a cell-capturing means which has a viscosity of not more than 500 mPa·s and not less than 5 mPa·s.

BEST MODE FOR CARRYING OUT THE INVENTION

Figure 1:
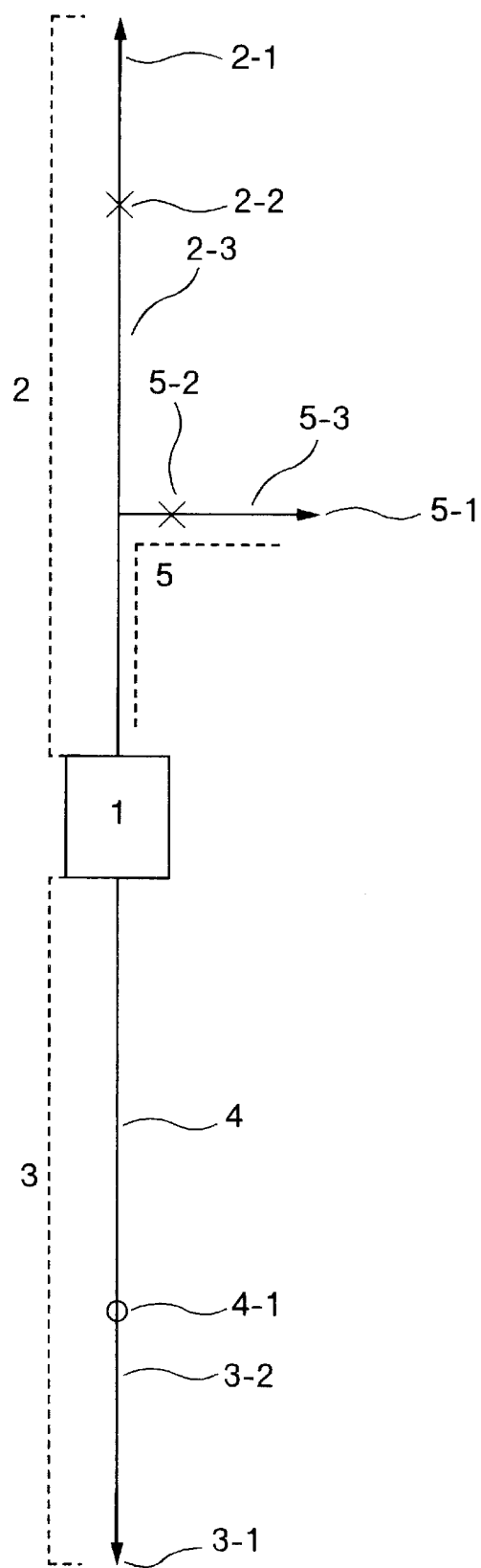
FIG. 1 is one embodiment of the cell separation system according to the present invention.

In the present specification, the term "cells to be recovered" means cells used for some purpose after their separation and recovery. The term "cells to be removed" means cells unnecessary for the above purpose or cells which should be positively removed because they are, for example, pathogenic cells, so that contamination by them of cells to be recovered causes a problem.

The cell-containing fluid containing cells to be recovered and cells to be removed can be but is not limited to peripheral blood, bone marrow, cord blood (including not only that collected through a umbilical cord blood vessel but also that collected through a placenta blood vessel), lymph fluids, and those obtained by subjecting the above fluids to some treatment such as centrifugation, and suspensions obtained by resuspending cells extracted from any of various organs or tissues, in some liquid.

The term "nucleated cells" means cells having a nucleus therein. The nucleated cells include, for example, leukocytes, granulocytes, neutrophils, baso-phils, eosinophils, myelocytes, erythroblasts, lymphocytes, T lymphocytes, helper T lymphocytes, cytotoxic T lymphocytes, suppressor T lymphocytes, B lymphocytes, NK cells, NKT cells, monocytes, macrophages, dendritic cells, osteoclasts, osteoblasts, osteocytes, hematopoietic stem cells, fibroblasts and chondroblasts.

The term "mononuclear cell fraction containing hematopoietic stem cells" means a mononuclear cell population containing hematopoietic stem cells and/or hematopoietic progenitor cells (they are hereinafter given the general name "hematopoietic stem cells"). "Mononuclear cell" is a general term for cells having a nucleus therein, and specific examples thereof are lymphocytes (T cells, B cells and NK cells), monocytes, hematopoietic stem cells, myelocytes, blast cells, etc.

The content of hematopoietic stem cells in the mononuclear cell population is usually 0.01% to 99% and varies depending on the kind of a starting cell population, and whether cells are treated or not. The content of hematopoietic stem cells is usually, for example, about 0.01% in peripheral blood, 0.05 to 1.0% in cord blood and 0.5 to 2% in bone marrow in the case of a normal person. In peripheral blood having a granulocyte colony-stimulating factor (G-CSF) administered, the content of hematopoietic stem cells differs markedly among individuals, and is 0.1 to several per cent. When cell separation using a monoclonal antibody, in particular, cell separation by a flow cytometry method is carried out, the content of hematopoietic stem cells reaches 99% in some cases. In any case, the term "mononuclear cell fraction containing hematopoietic stem cells" does not concretely specify the content of hematopoietic stem cells at all.

The cells having no nucleus which are referred to in the present specification include, for example, erythrocytes and platelets.

The expression "cells to be removed have a surface marker different from that of cells to be recovered" in the present specification means that the cells to be recovered and the cells to be removed are similarly nucleated cells, but are different in surface marker (the cells to be recovered and the cells to be removed belong different subgroups, respectively). For example, the cells to be recovered are helper T lymphocytes (having anti-CD4 antigen as a surface marker), and the cells to be removed are suppressor T lymphocytes (having anti-CD8 antigen as a surface marker).

When cells to be recovered are nucleated cells, and cells to be removed are cells having no nucleus, examples of their combination and examples of use thereof are as follows, but the combination and use are not limited thereto.

1. Cells to be recovered: leukocytes, cells to be removed: erythrocytes, use: interferon preparation.
2. Cells to be recovered: lymphocytes, cells to be removed: erythrocytes and platelets, use: adoptive-immuno therapy.
3. Cells to be recovered: a mononuclear cell fraction containing hematopoietic stem cells, cells to be removed: erythrocytes and platelets, use: hematopoietic stem cell transplantation.

When cells to be recovered are nucleated cells, and cells to be removed are nucleated cells having a surface marker different from that of the cells to be recovered, examples of their combination and examples of use thereof are as follows, but the combination and use are not limited thereto.

1. Cells to be recovered: CD34-positive nucleated cells, cells to be removed: CD34-negative nucleated cells, use: CD34-positive cell transplantation.
2. Cells to be recovered: CD8-positive T lymphocytes, cells to be removed: CD8-negative T lymphocytes, use: adoptive-immuno therapy.

When cells to be recovered are nucleated cells and cells to be removed are cells having no nucleus and nuleated cells having a surface marker different from that of the cells to be recovered, examples of their combination and examples of use thereof are as follows, but the combination and use are not limited thereto.

1. Cells to be recovered: CD34-positive nucleated cells, cells to be removed: erythrocytes, platelets and CD34-negative nucleated cells, use: CD34-positive cell transplantation.
2. Cells to be recovered: CD8-positive T lymphocytes, cells to be removed: erythrocytes, platelets and CD8-negative T lymphocytes, use: adoptive-immuno therapy.

In the present invention, the cell-capturing means capable of capturing at least cells to be recovered and substantially permitting passage therethrough of cells to be removed, may comprise a container having a liquid inlet and a liquid outlet which is packed with a material capable of capturing the cells to be recovered and substantially permitting passage therethrough of the cells to be removed, and a molded container having a cell-capturing surface on its inner surface. The material capable of not capturing the cells to be recovered and substantially permitting passage therethrough of the cells to be removed may be any conventional cell-capturing material so long as it can selectively capture the cells to be recovered. The following materials, for example, are preferable because of their excellent moldability, sterilizability, and low cytotoxicity: synthetic polymers such as polyethylenes, polypropylenes, polystyrenes, acrylic resins, nylons, polyesters, polycarbonates, polyacrylamides, polyurethanes, etc.; natural polymers such as agarose, cellulose, cellulose acetate, chitin, chitosan, alginates, etc.; inorganic materials such as hydroxyapatite, glass, alumina, titania, etc.; and metals such as stainless steel, titanium, aluminum, etc.

These capturing materials may be used as they are, or after being subjected to surface modification necessary for selective passage or capture of cells, etc. For example, for improving the permeability to platelets, there is, for instance, the method comprising coating with a polymer having nonionic hydrophilic groups and basic nitrogen-containing functional groups which has been proposed in International Publication No. WO 87/05812. As a method for selective capture of cells, a method of immobilizing a ligand having affinity for specific cells, such as an amino acid, peptide, sugar or glycoprotein (including bio-ligands such as antibody and adhesion molecules) may be used, for example, by the haloaceamide method proposed in JP-A-2-261833.

The shape of the capturing material may be granular, a fiber mass, woven fabric, nonwoven fabric, a spongy structure, a flat plate, etc. The granules, fiber mass, woven fabric, nonwoven fabric and spongy structure are preferable because they have a large surface area per volume. From the viewpoint of ease of handling, porous structures such as the fiber mass, woven fabric, nonwoven fabric and spongy structure are more preferable. Among them, the nonwoven fabric and spongy structure are the most preferable from the viewpoint of the flowability of a cell suspension and productivity.

When the nonwoven fabric is used, its fiber diameter in the case of not immobilizing a so-called bio-ligand capable of specifically binding to specific cells, such as anti-CD34 monoclonal antibody on the fabric surface, is usually not more than 30 $\mu$m and not less than 1.0 $\mu$m, preferably not more than 20 $\mu$m and not less than 1.0 $\mu$m, more preferably not more than 10 $\mu$m and not less than 1.5 $\mu$m. When the fiber diameter is less than 1.0 $\mu$m, the cells to be recovered are undesirably liable to be tightly captured and become difficut to recover. When the fiber diameter is more than 30 $\mu$m, the cells to be recovered are very likely to pass through the nonwoven material without being captured by fiber. Both of such values are not desirable because they tend to decrease the recovery.

When the spongy structure is used, its pore size is usually not more than 25 $\mu$m and not less than 2.0 $\mu$m, preferably not more than 20 $\mu$m and not less than 3.0 $\mu$m, more preferably not more than 15 $\mu$m and not less than 4.0 $\mu$m. When the pore size is less than 2.0 $\mu$m, the flowability is very low, so that the passage of a fluid through the spongy structure tends to be difficult in itself. When the pore size is more than 25 $\mu$m, the capture rate of the cells to be recovered is undesirably decreased, resulting in a low recovery.

The container packed with material capable of capturing the cells to be recovered and substantially permitting passage therethrough of the cells to be removed preferably uses, but is not limited to the following materials, for example, because of their excellent moldability, sterilizability, and low cytotoxicity: synthetic polymers such as polyethylenes, polypropylenes, polystyrenes, acrylic resins, nylons, polyesters, polycarbonates, polyacrylamides, polyurethanes, poly(vinyl chloride)s, etc.; inorganic materials such as hydroxyapatite, glass, alumina, titania, etc.; and metals such as stainless steel, titanium, aluminum, etc.

The molded container having a cell-capturing surface on its inner surface, i.e., an example of the cell-capturing means which is other than the container packed with the cell-capturing material, may be a flask, dish, conical tube, syringe, blood bag, etc.

In the present specification, the expression "substantially capturing cells to be recovered" means capturing 60% or more of cells to be recovered in a cell-containing fluid. The expression "substantially permitting passage therethrough of cells to be removed" means passing 60% or more of cells to be removed in the cell-containing fluid.

In the present invention, cells to be recovered which have been captured by the cell-capturing means are recovered by using a liquid with a specific viscosity (hereinafter referred to also as "recovering liquid" or "liquid for recovery"). The viscosity of this liquid should not be more than 500 mPa·s and not less than 5 mPa·s, preferably not more than 100 mPa·s and not less than 5 mPa·s, more preferably not more than 50 mPa·s and not less than 7 mPa·s. When the viscosity is less than 5 mPa·s, the recovery is low. When the viscosity is more than 500 mPa·s, the passage of the liquid through the cell-capturing means is very difficult even if a pump is used, so that the work-efficiency is low. Moreover, a pressure increase is caused, so that leakage from a joint between tubes in a line tends to occur. Therefore, such viscosity values are not desirable. As a method for measuring the viscosity, use of a rotating viscometer is preferable because it is the simplest, and has a high precision.

Any liquid may be used as the recovering liquid, so long as it has little undesirable influence on cells. For example, solutions of synthetic polymers such as poly(ethylene glycol)s poly(vinylpyrrolidone)s, poly(vinyl alcohol)s etc.; solutions of natural polymers such as methyl cellulose, gelatin, hydroxyethyl starch, dextran, chitin derivatives, collagen, fibronectin, albumin, globulin, etc.; solutions of organic substances such as glucose, saccharose, maltose, trehalose, sorbitol, glycerol, dimethyl sulfoxide, silicone oil, etc.; and mixtures thereof may be used. As a result of investigation by the present inventors, it was found that an especially high recovery can be attained by using dextran. Therefore, employment of dextran is explained below in detail.

The dextran referred to herein is a glucose polymer in which most of the glucose units are joined by $\alpha$-1,6 linkages. The dextran includes its partial hydrolysis products and its derivatives such as sulfate esters. Although the dextran is not limited in molecular weight, its average molecular weight is preferably 1,000 to 10,000,000, more preferably 5,000 to 5,000,000, most preferably 10,000 to 1,000,000, in view of solubility, availability, etc. Since the viscosity varies depending on the molecular weight, even at the same concentration, the molecular weight of the concentration is properly adjusted so that the viscosity may be not more than 500 mPa·s and not less than 5 mPa·s. A sterilized dextran 40 injection (a 10 w/v % solution of dextran with a molecular weight of about 40,000 in physiological saline), approved as a medicine, is on the market and hence can be suitably used. In order to adjust the viscosity to not more than 500 mPa·s and not less than 5 mPa·s, the dextran may be used singly, or in admixture with other substances. Examples of the substances are synthetic polymers such as poly(ethylene glycol)s, poly(vinyl-pyrrolidone)s, poly(vinyl alcohol)s, etc.; natural polymers such as methyl cellulose, gelatin, hydroxyethyl starch, dextran, chitin derivatives, collagen, fibronectin, albumin, globulin, etc.; and organic substances such as glucose, saccharose, maltose, trehalose, sorbitol, glycerol, dimethyl sulfoxide, etc. Although a mechanism by which cells can be recovered with high recovery by using dextran is not known at present, the present inventors conjecture that the dextran has a property of reducing the adhesiveness of the cells to the capturing material.

The solvent used for dissolving a solute in the preparation of the liquid having a viscosity of not more than 500 mPa·s and not less than 5 mPa·s, may be physiological saline, buffer solutions such as Dulbecco phosphate buffer solution (D-PBS), Hank's Balanced Salt Solution (HBSS) and the like, and media such as RPMI1640 and the like. If necessary, dextran, hydroxyethyl starch, albumin, globulin, glucose, saccharose, trehalose, globulin, citrate-phosphate-dextrose (CPD), acid-citrate-dextrose (ACD), EDTA, heparin, etc. may be incorporated into the liquid for supply of a nutriment, protection of cell membrane, or impartment of anticoagulating effect, etc.

The liquid with a specific viscosity according to the present invention is preferably one which can be used for cryopreservation of cells to be recovered, or preservation of the cells in a liquid state. As described above, for hematopoietic stem cell transplanation, in particular, hematopoietic stem cell transplanation using cord blood, a cell population freed of erythrocytes by a Ficoll method or the like is washed (because a Ficoll solution is toxic), and a cryoprotectant and the like are added thereto to prepare a cell suspension, followed by cryopreservation in liquid nitrogen or a freezer until needed for practical use. In the present invention, a cell suspension to be preserved can be prepared without troublesome operations after cell separation by using a liquid suitable both for the preservation, in particular, cryopreservation, as well as for recovery, by having a specific viscosity. Specific examples of the liquid for recovery which is usable for cryopreservation and as a cryoprotectant are, a nutriment, or a cell membrane protecting component, etc. Cryoprotectants are classified into two categories, 1) extracellular cryoprotectants, and 2) intracellular cryoprotectants, according to the action mechanism. In the first category, water-soluble polymers such as hydroxyethyl starch, dextran, poly(vinylpyrrolidone)s, etc. are generally used. In the second category, low-molecular weight organic compounds such as dimethyl sulfoxide, glycerol, etc. are generally used. The nutriment includes sugars such as glucose and the like, and various media for cell culture. As the cell membrane protecting component, albumin is generally used. Plasma is used in some cases as a combination of the nutriment and the cell membrane protecting component. As described above, these components are preferably used singly, or in combination in the liquid for recovery having a specific viscosity of the present invention. The components described above may be added at the time of cryopreservation after cell recovery.

There are generally two freezing methods employed, i.e., a simple method using a deep-freezer at $-80°$ C., or a method comprising slow cooling in a program freezer and preservation in liquid nitrogen. For thawing cells subjected to cryopreservation, rapid thawing in a warm bath at 37° C. is generally carried out.

As a method for introducing the cell-containing fluid referred to in the present specification into the cell-capturing means, there may be adopted either a method of connecting a bag or bottle containing the cell-containing fluid through a tube, and then introducing the fluid, for example, by utilizing its fall, a roller pump, causing a flow of the fluid by squeezing the bag, or by a method of connecting a syringe containing the cell-containing fluid, and introducing the fluid by pushing the piston of the syringe by hand or using a device such as a syringe pump. The pushing by hand is characterized by its simplicity, and the use of the device is characterized in that the control of the flow rate of the recovering liquid in its introduction is easy. Therefore, a suitable method is selected depending on the purpose.

When the cell-containing fluid is introduced into the cell-capturing means, the cells to be recovered are captured, and the cells to be removed flow out, but a minority thereof remain in the container in some cases.

Therefore, the cell-capturing means is preferably rinsed in order to rinse away the slight amount of the remaining cells to be removed. Any rinse may be used, so long as it is a physiological solution. Several examples thereof are physiological saline, buffer solutions such as Dulbecco phosphate buffer solution (D-PBS), Hank's Balanced Salt Solution (HBSS) and the like, and media such as RPMI1640 and the like. If necessary, dextran, hydroxyethyl starch, albumin, globulin, glucose, saccharose, trehalose, globulin, citrate-phosphate-dextrose (CPD), acid-citrate-dextrose (ACD), EDTA, or heparin, etc. may be added to the physiological solutions mentioned above for supply of a nutriment, protection of cell membrane, and impartment of anticoagulating effect, etc.

There are two directions for introduction of the rinse, i.e., the same direction as the direction of introduction of the cell-containing fluid, and the direction opposite thereto. Of these, the same direction is preferable. In the case of the opposite direction, the cells to be recovered which have been captured are liable to leak out owing to the rinsing. The viscosity of the rinse is preferably less than 5 mPa·s. When the viscosity is 5 mPa·s or more, the cells to be recovered which have been captured are liable to leak out.

In the present invention, as a method for introducing the liquid with a viscosity of not more than 500 mPa·s and not less than 5 mPa·s into the above-mentioned cell-capturing means, there may be adopted either a method of connecting a bag or bottle containing the liquid to the cell-capturing means through a tube, and introducing the liquid by utilizing its fall, a roller pump, by squeezing the bag, or by a method of connecting a syringe containing the liquid, and introducing the liquid into the cell-capturing means by pushing the piston of the syringe by hand, or by using a device such as a syringe pump. In this case, as in the direction of introduction of the liquid, there are two directions, i.e., the same direction as the direction of introduction of the cell-containing fluid, and the direction opposite thereto. Of these, the latter is usually preferable because the cell recovery is higher. The flow rate of the recovering liquid is preferably rapid because the recovery tends to be increased. The linear speed obtained by dividing the flow rate by the filtration sectional area is usually 0.5 cm/min. or more, preferably 5 cm/min. or more, and more preferably 10 cm/min. or more.

It is also possible to recover a slight amount of cells (or their constituents) remaining in the cell-capturing means, by introducing another liquid after introducing the recovering liquid. By this recovery, the collection of a sample for HLA typing, which is indispensable, for example, in hematopoietic stem cell transplantation, can be carried out simultaneously with the cell separation procedure. A slight amount of the cells (or their constituents) remaining in the cell-capturing means are used for various purposes, other than HLA typing such as investigation of ex vivo expansion of hematopoietic stem cells, genetic diagnosis, or employment in cell transplantation in combination with the cells obtained by the first recovery. A brief supplementary explanation of HLA typing is given below.

HLA typing is carried out by using DNA present in the nuclei of nucleated cells. Therefore, recovering the DNA is preferable to recovering the cells themselves because it is laborsaving. Accordingly, a liquid capable of lysing or disrupting the cells is preferably used as a recovering liquid. The liquid includes, for example, hypotonic liquids such as solutions of surfactants (e.g. sodium dodecyl sulfate, lauryl sodium sulfate and Triton X-100), distilled water, ion-exchanged water, etc. The DNA recovered by the use of such a liquid is purified by a well-known phenol chloroform method or the like and subjected to HLA typing.

In the present invention, the recovered cells may be preserved until use. For the preservation, there are two methods, preservation in a liquid state, and cryopreservation. The cryopreservation is usually carried out because the preservation in a liquid state is limited in time to at most 2 to 3 days in the case of, for example, hematopoietic stem cells.

Next, the cell separation system of the present invention is explained below. The line referred to in the present specification, i.e., the line for introducing the cell-containing fluid into the cell-capturing means which is connected upstream to the inlet of the cell-capturing means is a line connectable to, for example, a container reserving the cell-containing fluid, or a line connectable to a living body tissue in which the cell-containing fluid is present. Specific examples of the former are as follows: a tube equipped with a spike or a tube equipped with a Luer adapter (male or female) is properly selected when the container reserving the cell-containing fluid is a blood bag, or a mere tube is properly selected when connection by a sterilized connector (hereinafter referred to as "SCD connection") is made. In addition, a tube having a septum is properly selected as the line when the container reserving the cell-containing fluid is a syringe equipped with a needle, or a Luer adapter (female) is properly selected as the line when the container is a syringe having a Luer opening but not a needle. Specific examples of the latter line are as follows, for example, when cord blood is used, the aforesaid living body tissue is umbilical cord and/or placenta, and a tube equipped with a metallic needle stickable into them is mentioned as the latter line. When a tube is used, it may be equipped between its ends with a clamp for opening or shutting the line, a roller clamp for adjusting the flow rate, a mesh chamber for removing aggregates, a syringe for giving the flow rate (including a flow path changing means), etc. When a syringe is used, it may be directly connected to the inlet of the cell-capturing means without a tube.

The other line referred to in the present specification, i.e., the line for introducing a liquid into the aforesaid cell-capturing means which is connected downstream to the outlet of the aforesaid cell-capturing means, includes lines which are classified as follows according to whether a container containing the liquid to be introduced into the cell-capturing means has been previously connected or is subsequently connectable, and according to the means used for introducing the liquid. That is, when the container containing the liquid to be introduced into the cell-capturing means is previously connected, the line includes, for example, a tube equipped with a bag, and a syringe. In the case of such a bag, a method for introducing the liquid into the cell-capturing means includes a method utilizing the fall of the liquid, a method of squeezing the bag, a method using a roller pump, etc. When the container containing the liquid to be introduced into the cell-capturing means is connected afterwards, the following tubes are selected. When a syringe is used, the line includes a needlable tube having a septum, a tube equipped with a Luer adapter (female), a tube equipped with a three-way stopcock, etc., to which the syringe can be connected. When a bag is used, a line connectable to the bag, i.e., a tube equipped with a spike, or a tube equipped with a Luer adapter (male or female) is properly selected as the aforesaid line. When SCD connection is made, a mere tube is properly selected as the aforesaid line. When a syringe is used, it may be directly connected to the outlet of the cell-capturing means without a tube.

The other line referred to in the present specification, i.e., the line for recovering cells from the inlet side of the aforesaid cell-capturing means which is connected upstream to the inlet of the aforesaid cell-capturing means, includes lines which are classified as follows according to a container for recovering cells which flow out of the cell-capturing means. That is, when the cells are recovered into a bag, a line connected or connectable to the bag, i.e., a tube equipped with a spike or a tube equipped with a Luer adapter (male or female) is properly selected as the aforesaid line. When SCD connection is made, a mere tube is properly selected as the aforesaid line. When the cells are collected into a conical tube, any open-ended line may be used. When the cells are collected by using a syringe having a Luer opening, a Luer adapter (female), a three-way stopcock and the like are used. When a syringe is used, it may be directly connected to the inlet of the cell-capturing means without a tube.

Instead of this other line, for example, a container for recovering the cells which flow out of the cell-capturing means is preferably able to withstand freezing and thawing, such as a freeze bag, because the transfer of the cells to a freeze bag can then be omitted. Examples of cryopreservation bags are freeze bags such as "Cryocyte" manufactured by Baxter, "Cell Freeze Bag" manufactured by Charter Med, "Hemo Freeze Bag" manufactured by NPBI, etc.

To the cell separation system according to the present invention, a line for introducing a liquid into the cell-capturing means may be added in order to rinse away a slight amount of cells to be removed which remain in the cell-capturing means, before recovering cells captured by the cell-capturing means. This line includes lines which are classified as follows according to whether a container containing the liquid is previously connected, or subsequently connectable, and according to the means for introducing the liquid. That is, when the container containing the liquid is previously connected, the line includes, for example, a tube equipped with a bag, and a syringe. When the container containing the liquid is connected afterwards, the following types of tubes are selected. When a syringe is used, the line includes a needlable tube having a septum, and a tube equipped with a Luer adapter (female), to which the syringe can be connected. When a bag is used, a line connectable to the bag, i.e., a tube equipped with a spike or a tube equipped with a Luer adapter (male or female) is properly selected as the line. When an SCD connection is made, a mere tube is properly selected as said line. When a syringe is used, it may be directly connected to the outlet of the cell-capturing means without a tube. Although the position of connecting said line to the cell-capturing means may be on either the inlet side or the outlet side, it is preferably on the inlet side from the viewpoint of ease of operation.

The present cell separation system, may have a line added for collecting cells (or their constituents) remaining in the cell-capturing means by further introducing a liquid after recovering cells to be recovered. In the case where cells different in purpose of use from the first recovered cells are recovered, for example, in the case where a solution capable of lysing or disrupting cells is used for collecting cells (or their constituents) remaining in the cell-capturing means for HLA typing, the line should comprise a means for changing the flow path, and a plurality of branches so that the cells (or their constituents) collected afterward will not be mixed with the first recovered cells. The flow path changing means may include clamps, spikes, etc.

The cell separation method using the abovementioned line system comprises steps of introducing, through a line connected upstream, a cell-containing fluid containing cells to be recovered and cells to be removed into a cell-capturing means capable of substantially capturing the cells to be recovered and substantially permitting passage of the cells to be removed. The resulting fluid containing the cells to be removed is taken out through the outlet of the cell-capturing means, and then a liquid with a viscosity of not more than 500 mPa·s and not less than 5 mPa·s is introduced into the cell-capturing means through a line connected downstream from the outlet of the cell-capturing means in order to recover the cells. When the recovered cells are preserved, the line (e.g. a freeze bag) connected upstream to the inlet of the cell-capturing means and containing the cells recovered, is sealed up and separated. The sealing-up and separation are carried out, for example, as follows: the line is sealed up by heat fusion using a heat sealer or the like, and then cut off, or a tube connected through a Luer adapter is detached from the main body and then heat-fused by using a heat sealer or the like. In any case, the term "sealing-up and separation" does not specify the order of operations (e.g. sealing-up followed by separation) at all.

The present invention further provides a liquid which contains hematopoietic stem cells which is substantially free from erythrocytes and/or platelets, and has a viscosity of not more than 500 mPa·s and not less than 5 mPa·s. The expression "substantially free from" used here means that this cell-containing fluid is prepared by removing 60% or more of erythrocytes and/or platelets from a starting cell-containing fluid. Although cord blood contains erythrocytes in addition to hematopoietic stem cells, a hematopoietic stem cell suspension containing substantially no erythrocyte can be provided by employing the cell separation method of the present invention. Furthermore, the cell-containing fluid may contain a cryopreservative agent.

The present invention still further provides a liquid containing cells to be recovered and substantially no cells to be removed which is obtained by a cell separation method comprising steps of introducing a cell-containing fluid containing cells to be recovered and cells to be removed, into a cell-capturing means capable of substantially capturing said cells to be recovered and substantially permitting passage there through of said cells to be removed. The resulting fluid containing the cells to be removed is taken out of the cell-capturing means, and then a liquid with a viscosity of not more than 500 mPa·s and not less than 5 mPa·s is introduced into the cell-capturing means to recover the cells which have been captured by the cell-capturing means. When the separation method of the present invention is applied to a suspension containing cells to be recovered and cells to be removed, it becomes possible to efficiently provide a suspension substantially comprising the cells to be recovered.

The present invention still further provides a liquid with a viscosity of not more than 500 mPa·s and not less than 5 mPa·s as a liquid for recovering captured cells from a cell-capturing means. This liquid is preferably one which can be used also as a preservative for cells. In the case of preservation in a liquid state, specific examples of the preservative are sugars (e.g. glucose), nutriments (e.g. various media for cell culture), cell membrane protecting components (e.g. albumin), and combinations of a nutrient and a cell membrane protecting component (e.g. plasma). In the case of cryopreservation, the preservative includes cryoprotectants, in addition to the above examples. The cryoprotectants are classified into two categories, 1) extracellular cryoprotectants, and 2) intracellular cryoprotectants, according to the action mechanism. In the first category, water-soluble polymers such as hydroxyethyl starch, dextran, and poly(vinylpyrrolidone)s, etc. are generally used. In the second category, low-molecular weight organic compounds such as dimethyl sulfoxide, and glycerol, etc. are generally used.

An embodiment of the cell separation system according to the present invention is explained below with reference to the drawings, which should not be construed as limiting the scope of the invention.

FIG. 1 shows one embodiment of the cell separation system according to the present invention. In this system, all of the following connections are made by the use of spikes: the connection of a starting-cell bag (containing a cell-containing fluid containing cells to be recovered and cells to be removed) to the main body of the system of the present invention; the connection of a bag for recovering a fluid which flows out through the outlet of a cell-capturing means, to the main body of the system of the present invention; and the connection of a bag for recovering cells from the outlet side of the cell-capturing means, to the main body of the system of the present invention. In the system, there is a three-way stopcock provided to which a syringe with a male Luer opening is connected for introducing a liquid into the cell-capturing means.

In FIG. 1, numeral 1 denotes the cell-capturing means capable of substantially capturing the cells to be recovered and substantially permitting passage there through of the cells to be removed. Numeral 2 denotes a line for introducing the cell-containing fluid into the cell-capturing means from the starting-cell bag, which comprises a spike 2-1, a clamp 2-2 and a tube 2-3. Numeral 3 denotes a line for discharging the fluid which flows out through the outlet of the cell-capturing means 1, which comprises a spike 3-1 and a tube 3-2. Numeral 4 denotes a line for introducing the liquid into the cell-capturing means from the outlet side of the cell-capturing means 1, which shares the tube with the line 3 and has the three-way stopcock 4-1 to which the syringe is connected. Numeral 5 denotes a line for recovering cells from the inlet side of the cell-capturing means, which comprises a spike 5-1, clamp 5-2, a tube 5-3 and a part of the tube 2-3. This line shares the tube 2-3 with the line 2 from the inlet of the cell-capturing means 1 to the point at which the tube 5-3 diverges from the tube 2-3.

Next, a method for using the cell-capturing means is explained below. Initially, the clamp 2-2 is shut, the three-way stopcock 4-1 is closed only in the direction of syringe connection, and the clamp 5-2 is closed. Then, the spike 2-1 is stuck into the starting-cell bag and the spike 3-1 is stuck into an empty bag. When the clamp 2-2 is opened, the cell-containing fluid is supplied to the cell-capturing means 1 through the tube 2-3 of the line 2. The cells to be recovered are captured and the cells to be removed are taken out and then collected in the empty bag through the tube 3-2 of the line 3. After completion of the treatment of the cell-containing fluid, the clamp 2-2 is closed, and the spike 2-1 is pulled out of the starting-cell bag and stuck into a commercially available bottle of physiological saline. When the clamp 2-2 is opened, the physiological saline rinses the cell-capturing means 1 and is collected in the bag containing the collected cells to be removed, through the line 3. After completion of the rinsing, the clamp 2-2 and the tube 3-2 are closed. Subsequently, a syringe containing a liquid with a viscosity of not more than 500 mPa·s and not less than 5 mPa·s is connected to the three-way stopcock 4-1, and the spike 5-1 is stuck into a cell-recovering bag. The three-way stopcock is turned in such a direction that the syringe communicates only with the cell-capturing means 1. After the clamp 5-2 is opened, the piston of the syringe is pushed to introduce the liquid into the cell-capturing means 1 from its outlet side, whereby the cells captured by the cell-capturing means are recovered into the cell-recovering bag through the line 5.

The present invention is illustrated below in further detail with reference to examples, which should not be construed as limiting the scope of the invention.

EXAMPLE 1

This working example shows an example of cell separation in the case where a cell-containing fluid was cord blood, cells to be recovered are a mononuclear cell fraction containing hematopoietic stem cells, and cells to be removed are erythrocytes and platelets.

① Cell Separator

A polycarbonate container with outside dimensions (length×width×thickness) of 41×41×18 mm having a liquid outlet and a liquid inlet on the diagonal was packed with 12 polyester nonwoven fabrics with an average fiber diameter of 2.3 μm on the inlet side and 25 polyester nonwoven fabrics with an average fiber diameter of 12 μm on the outlet side. The packing density was 0.24 g/cm$^3$, the effective filtration area 9 cm$^2$, and the effective filtration length 12.4 mm. In order to impart platelet permeability to the resulting filter, coating with a hydrophilic polymer was carried out. In detail, a 1% ethanolic solution of a hydroxyethyl methacrylate dimethylaminoethyl methacrylate copolymer (molar ratio between hydroxyethyl methacrylate and dimethylaminoethyl methacrylate=97:3) was passed through the filter from the inlet side of the filter, after which the filter was dried by introducing nitrogen gas thereinto.

② Preparation of a Recovering Liquid

A commercially available solution of dextran 40 in physiological saline (Dextran 40 Injection-Midori, a trade name, available from Green Cross Corp.) was incorporated with human serum albumin to prepare a liquid containing 4% human serum albumin as recovering liquid A. This recovering liquid A was diluted 1.2-fold or 1.3-fold with physiological saline to obtain recovering liquid B and recovering liquid C, respectively. The viscosities of the recovering liquids are as follows: recovering liquid A 10.5 mPA·s, recovering liquid B 8.0 mPA·s, recovering liquid C 5.3 mPA·s.

③ Cell Separation Procedure and Line System

200 Milliliters of cord blood collected from a placenta and umbilical cord after delivery and containing 15 vol % CPD was divided into four portions, and an experiment was carried out at 4 recovering liquid viscosity values (including that in Comparative Example 1) by using the same blood divided.

Figure 2:
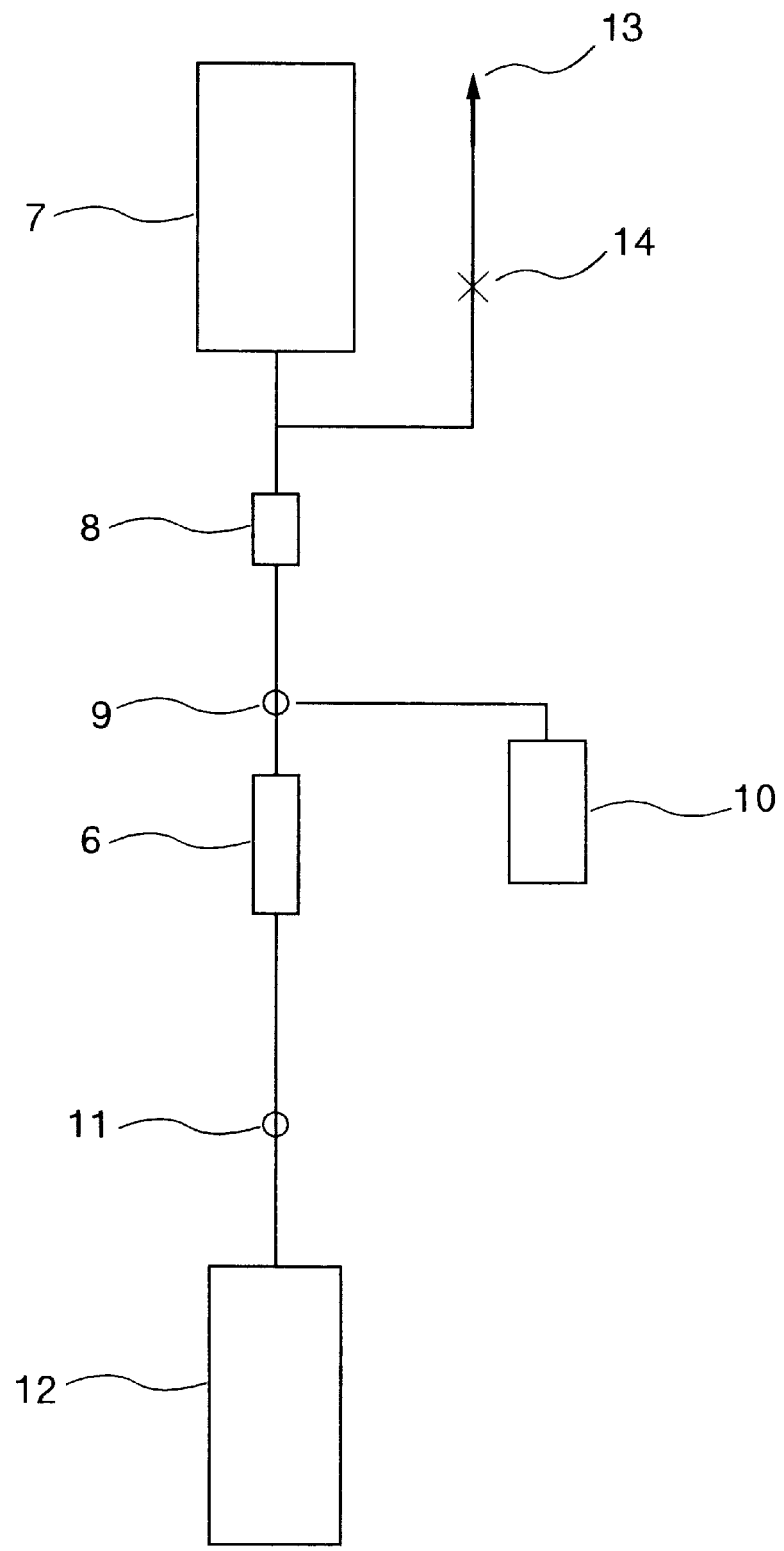
FIG. 2 is a schematic view of a cell separation system used in Example 1.

As shown in FIG. 2, a blood bag was connected to the inlet side of the cell separator 6 produced in the above item ①, through a tube having between its ends a three-way stopcock 9 having a bag for cell recovery 10 connected thereto, a mesh chamber 8, and a diverging point to a tube equipped with a spike 13 to be connected to a bottle of physiological saline for rinsing. A drain bag 12 was connected to the outlet side of the cell separator 6 through a tube having between its ends a three-way stopcock 11 for connecting a syringe for recovery.

A fluid containing nucleated cells in the starting-blood bag 7 was introduced into the cell separator at a head of about 60 cm, and a fluid containing erythrocytes and platelets which had flowed out of the cell separator 6 was discharged into the drain bag 12. Then, the spike 13 was stuck into the bottle of physiological saline, and the clamp 14 was opened, whereby the inside of the filter was rinsed with about 20 ml of physiological saline to rinse away a slight amount of erythrocytes and platelets, which remained in the filter. Subsequently, a 30-ml disposable syringe containing 25 ml of each recovering liquid was connected to the three-way stopcock 11, and the three-way stopcock 11 was turned in such a direction that the syringe communicated only with the cell separator. The three-way stopcock 9 was turned in such a direction that the cell separator 6 communicated only with the bag for cell recovery 10. Then, the piston of the syringe was pushed to recover cells captured in the cell separator, into the bag for cell recovery 10.

④ Analysis

The number of nucleated cells, the number of mononuclear cells, the number of erythrocytes, and the number of platelets were determined with an automatic hemocytometer. The percentage of CD34-positive cells based on the total number of nucleated cells was measured by the use of FITC-labeled anti-CD34 antibody according to a flow cytometry method comprising display on SSC-FITC (Miyazaki et al. "Nichijo Shinryo to Ketsueki (Practical Hematology)" Vol. 5, No. 2, pp. 21–24, 1995).

The recovery and the removal rate were calculated by the following equations:

Recovery (%)=100×(number of recovered cells/number of cells in starting cell population)

Removal rate (%)=100−100×(number of recovered cells/number of cells in starting cell population)

⑤ Results

The time required for pushing the piston of the syringe completely was 3 seconds. The linear speed was calculated to be 55.6 cm/min. The results are summarized in Table 1. It can be seen that nucleated cells, mononuclear cells and CD34-positive cells could be recovered at high percentages in the cell suspension recovered, and that erythrocytes and platelets were removed at high percentages.

TABLE 1

| Recover- | Recovery (%) | | | Removal rate (%) | |
|---|---|---|---|---|---|
| ing liquid (mPa.s) | Nucleated cell | Mononuclear cell | CD34- positive cell | Erythro- cyte | Plate- let |
| A(10.5) | 75.2 | 90.2 | 97.0 | 99.0 | 88.0 |
| B(8.0) | 74.0 | 90.0 | 96.6 | 99.0 | 88.0 |
| C(5.3) | 73.0 | 89.6 | 95.5 | 99.0 | 88.0 |

The cells recovered by the use of the recovering liquid could be subjected to cryopreservation according to the protocol described in an instruction mannual for a cryopreservative agent "CP-1" manufactured by Kyokuto Pharmaceutical Industrial Co., Ltd. In detail, dimethyl sulfoxide was added to the recovered cell suspension to adjust its final concentration to 5%, and the resulting mixture was subjected to cryopreservation in a deep-freezer at −80° C. After 30 days of cryopreservation, the mixture was rapidly thawed in a warm bath at 37° C., and the cell viability was measured by a conventional trypan blue exclusion method and found to be maintained at a high value of 90.4%.

COMPARATIVE EXAMPLE 1

In this comparative example, results obtained by using a recovering liquid with a low viscosity containing no dextran were compared with those obtained in Example 1, though as in Example 1, a cell-containing fluid was cord blood, cells to be recovered are a mono-nuclear cell fraction containing hematopoietic stem cells, and cells to be removed are erythrocytes and platelets.

① Cell Separator

The same cell separator as in Example 1 was used.

② Cell Separation Procedure and Line System

One of the portions of the cord blood obtained in Example 1 was used as starting cord blood. The process of Example 1 was repeated except for using 25 ml of physiological saline as a recovering liquid. The same line system as in Example 1 was used. The viscosity of the recovering liquid was 1.0 mPa·s.

③ Analysis

The same analysis as in Example 1 was carried out.

④ Results

The time required for pushing the piston of the syringe completely was 3 seconds. The results are summarized in Table 2. The recoveries of nucleated cells, mononuclear cells and CD34-positive cells in the cell suspension recovered were lower than in Example 1.

TABLE 2

| Recover- | Recovery (%) | | | Removal rate (%) | |
|---|---|---|---|---|---|
| ing liquid (mPa.s) | Nucleated cell | Mononuclear cell | CD34- positive cell | Erythro- cyte | Plate- let |
| Physio- logical saline (1.0) | 31.0 | 40.0 | 45.0 | 99.0 | 89.7 |

EXAMPLE 2

This working example shows an example of cell separation in the case where a cell-containing fluid was peripheral blood, cells to be recovered are leukocytes, and cells to be removed are erythrocytes and platelets.

① Cell Separator

A polycarbonate container with outside dimensions (length×width×thickness) of 41×41×18 mm having a liquid outlet and a liquid inlet on the diagonal was packed with 25 polyester nonwoven fabrics with an average fiber diameter of 12 $\mu$m on the inlet side and 12 polyester nonwoven fabrics with an average fiber diameter of 2.3 $\mu$m on the outlet side. The packing density was 0.24 g/cm, the effective filtration area 9 cm$^2$, and the effective filtration length 12.4 mm. In order to impart platelet permeability to the resulting filter, coating with a hydrophilic polymer was carried out. A 1% ethanolic solution of a hydroxyethyl methacrylate•dimethylaminoethyl methacrylate copolymer (molar ratio between hydroxyethyl methacrylate and dimethylaminoethyl methacrylate=97:3) was passed through the filter from the inlet side of the filter, after which the filter was dried by introducing nitrogen gas thereinto.

② Cell Separation Procedure

Into the cell separator produced was introduced 50 ml of whole peripheral blood (containing 15 vol % CPD) of a healthy person through the liquid inlet by utilizing the head (about 60 cm; flow rate about 5 ml/min.). Thereafter, 30 ml of physiological saline was passed through the cell separator by means of head (about 60 cm) in order to rinse away erythrocytes and platelets, which remained in the cell separator. Then, 30 ml of a 3.5% solution of a poly (vinylpyrrolidone) (average molecular weight: 360,000) in physiological saline was introduced into the cell separator at a rate of 100 ml/min. through the liquid outlet by the use of a pump, and cells were recovered through the liquid inlet. The viscosity of this recovering liquid was 20.3 mPa·s.

③ Analysis

The number of leukocytes, the number of erythrocytes and the number of platelets were determined with an automatic hemocytometer.

④ Results

The results are summarized in Table 3. Leukocytes were recovered at a high percentage in the cell suspension recovered, and erythrocytes and platelets were removed at high percentages. The linear speed was calculated to be 11.1 cm/min.

TABLE 3

| Recovery (%) | Removal rate (%) | |
|---|---|---|
| Leucocyte | Erythrocyte | Platelet |
| 75.0 | 99.1 | 90.3 |

EXAMPLE 3

This working example shows an example of cell separation in the case where a cell-containing fluid was cord blood, cells to be recovered are hematopoietic stem cells (CD34-positive cells), and cells to be removed are erythrocytes and platelets.

① Cell Separator

A polycarbonate container with outside dimensions (length×width×thickness) of 41×41×18 mm having a liquid outlet and a liquid inlet on the diagonal was packed with 12 polyester nonwoven fabrics with an average fiber diameter of 12 μm on the inlet side and 25 polystyrene nonwoven fabrics with an average fiber diameter of 2.3 μm having anti-human CD34 monoclonal mouse antibody (clone name: Immu133, available from Coulter Corp.; hereinafter abbreviated as "CD34 antibody") immobilized thereon, on the outlet side. The packing density of the resulting filter was 0.2 g/cm$^3$. The immobilization of the anti-human CD34 monoclonal mouse antibody on the polystyrene was carried out by the well-known haloacetamide method proposed in JP-A-2-261833. In detail, polystyrene nonwoven fabrics (previously cut to the above-mentioned dimensions) were immersed in a treating solution prepared by adding 3.6 g of hydroxymethyliodoacetamide and 25 g of trifluoromethanesulfonic acid to 165 ml of sulfolane, at room temperature for 5 hours to be reacted, for the purpose of activating the polystyrene nonwoven fabrics. The nonwoven fabrics thus activated were washed with D-PBS, after which, in order to immobilize the antibody on them, they were immersed for 2 hours in 10 ml of a CD34 antibody solution having a concentration adjusted to 20 μg/ml with D-PBS, and they were washed with D-PBS and then freeze-dried, whereby the nonwoven fabrics having the antibody immobilized thereon were obtained.

② Preparation of a Recovering Liquid

A commercially available solution of dextran 40 in physiological saline (Dextran 40 Injection-Midori, a trade name, available from Green Cross Corp.) was incorporated with human serum albumin to prepare a liquid containing 4% human serum albumin as a recovering liquid. The viscosity of the recovering liquid was 9.8 mPA·s.

② Cell Separation Procedure

A blood bag containing 50 ml of fresh human cord blood (containing 15 vol % of an anticoagulant CPD) was connected to the inlet side of the cell separator produced in the above item ①, through a tube having between its ends, diverging points to a physiological saline bag and a bag for cell recovery, respectively. A blood bag for drain was connected to the outlet side of the cell separator through a tube having a three-way stopcock between the ends of the tube. Into the cell separator was introduced 50 ml of the fresh cord blood by utilizing its fall (about 60 cm), and an erythrocyte-containing fluid (also containing CD34-negative cells and platelets) which had flowed out of the filter was recovered into the drain bag. Then, 30 ml of physiological saline was passed through the filter in order to rinse away erythrocytes, platelets and CD34-negative cells, which remained in the filter.

Subsequently, a syringe containing 30 ml of the recovering liquid prepared in the above item ② was connected to the three-way stopcock of the tube on the outlet side of the cell separator, and the recovering liquid was introduced into the cell separator by pushing the piston of the syringe, to recover the captured cells into the bag connected to the inlet side.

③ Analysis

The same analysis as in Example 1 was carried out.

④ Results

The time required for pushing the piston of the syringe completely was 3 seconds. The linear speed was calculated to be 55.6 cm/min. The results are summarized in Table 4. It can be seen that CD34-positive cells could be recovered at a high percentage in the cell suspension recovered, and that erythrocytes, platelets and CD34-negative cells were removed at high percentages.

TABLE 4

| Recovery (%) | Removal rate (%) | | |
|---|---|---|---|
| CD34-positive cell | Erythrocyte | Platelet | CD34-negative cell |
| 78 | 99.2 | 90.4 | 90 |

EXAMPLE 4

This working example shows an example of cell separation in the case where a cell-containing fluid was cord blood, cells to be recovered are a mononuclear cell fraction containing hematopoietic stem cells, cells to be removed are erythrocytes and platelets, and DNA for HLA typing was collected at the same time.

① Cell Separator

The same cell separator as in Example 1 was used.

② Preparation of Recovering Liquids

A commercially available solution of dextran 40 in physiological saline (Dextran 40 Injection-Midori, a trade name, available from Green Cross Corp.) was incorporated with human serum albumin to prepare a liquid containing 4% human serum albumin as a first recovering liquid (for cell recovery). Distilled water for injection, and a hypotonic liquid was used as an additional recovering liquid (for recovering cell constituents). The viscosity of the first recovering liquid was 10.5 mPA·s.

③ Line System

Figure 3:
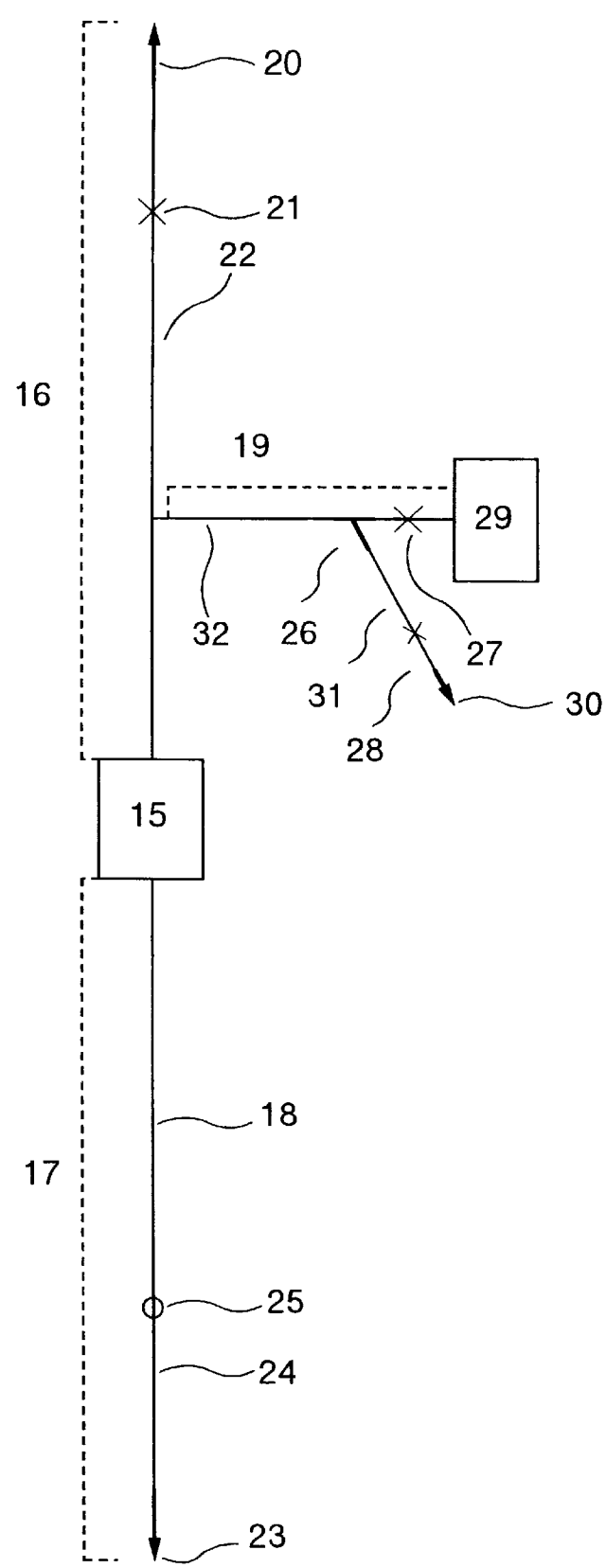
FIG. 3 is a schematic view of a cell separation system used in Example 4.

The cell separation system shown in FIG. 3 was obtained by incorporating the cell separator described in the above item ① into lines. In this system, the connection of a cell-containing fluid bag to the main body of the system of the present invention, and the connection of a bag for recovering a fluid which flows out through the outlet of the cell-capturing means, to the main body of the system of the present invention were made with spikes. A line for recovering cells from the inlet side of the cell-capturing means was equipped with a freeze bag for recovering cells for cell transfer, and a tube with a spike at the end for recovering DNA for HLA typing into a conical tube. In this line, the flow paths are changed by means of clamps.

④ Cell Separation Procedure

A cell separation procedure was carried out by using the line system shown in FIG. 3.

Initially, clamp 21 was shut, a three-way stopcock 25 was shut only in the direction of syringe connection, and clamps 27 and 28 were shut.

A spike 20 was stuck into a blood bag containing 50 ml of fresh human cord blood (containing 15 vol % of an anticoagulant CPD), and a spike 23 was stuck into an empty bag. When the clamp 21 was opened, the cell-containing fluid was supplied to the cell-capturing means through the tube 22 of a line 16, and a mononuclear cell fraction containing hematopoietic stem cells was captured, and erythrocytes and platelets were discharged into the empty bag through the tube 24 of a line 17.

After completion of the treatment of said cell-containing fluid, the clamp 21 was shut and the spike 20 was pulled out, and then stuck into a commercially available 100-ml bottle of physiological saline. When the clamp 21 was opened, the physiological saline rinsed away a slight amount of erythrocytes and plate-lets, which remained in the cell-capturing means 15, and the physiological saline was discharged through the line 17. Then, the clamp 21 was shut. Next, a 30-ml syringe containing 25 ml of the recovering liquid prepared in the above item ② was connected to the three-way stopcock 25, after which the three-way stopcock 25 was turned in such a direction that the syringe communicated only with the cell-capturing means 15 through a line 18, and the clamp 27 was opened. The piston of the syringe was pushed to recover cells into a freeze bag 29 through a line 19. Subsequently, the syringe was detached from the three-way stopcock 25, and another syringe containing 25 ml of distilled water for injection was connected to the three-way stopcock 25. The clamp 27 was shut, and clamp 28 was opened, being attached to a tube 31 capable of communicating with the tube 32 of the line 19 through a Y-tube 26. A conical tube was placed under a spike 30, after which the distilled water for injection was introduced into the cell-capturing means by pushing the piston of the syringe, to disrupt the captured cells, and crude DNA in these cells was recovered in the conical tube. The crude DNA recovered was purified by a conventional method comprising deproteination using proteinase K and phenol chloroform method.

⑤ Analysis

The numbers of cells were determined by the same method as described in Example 1. The amount of the purified DNA was determined by a conventional method comprising measuring absorbance at 260 nm by means of a spectrophotometer (Nakayama et al., Cell Technology, extra issue "Bio-experiment Illustrated" ① Fundamentals of Molecular Biological Experiment, 1995).

⑥ Results

The time required for pushing the piston of the syringe completely was 3 seconds. The linear speed was calculated to be 55.6 cm/min. The results are summarized in Table 5. It can be seen that eukaryotic cells, mononuclear cells and CD34-positive cells could be recovered at high percentages in the cell suspension recovered, and that erythrocytes and platelets were removed at high percentages. It can also be seen that the amount of the DNA obtained was about 10 μg, an amount sufficient for HLA typing.

TABLE 5

| Recovery (%) | | | Removal rate (%) | | Amount of purified DNA (μg) |
| --- | --- | --- | --- | --- | --- |
| Nucleated cell | Mononuclear cell | CD34-positive cell | Erythrocyte | Platelet | |
| 75.0 | 90.4 | 97.2 | 98.9 | 88.3 | 9.8 |

EXAMPLE 5

This working example shows an example of cell separation in the case where a cell-containing fluid was bone marrow, cells to be recovered are a mononuclear cell fraction containing hematopoietic stem cells, and cells to be removed are erythrocytes and platelets.

① Cell Separator

The same cell separator as in Example 1 was used.

② Preparation of a Recovering Liquid

A commercially available solution of dextran 40 in physiological saline (Dextran 40 Injection-Midori, a trade name, available from Green Cross Corp.) was incorporated with human serum albumin to prepare a liquid containing 4% human serum albumin as a recovering liquid. The viscosity of the recovering liquid was 10.1 mPA·s.

③ Cell Separation Procedure and Line System

As shown in FIG. 2, a blood bag containing 30 ml of bone marrow (containing 15 units/ml of an anticoagulant heparin) was connected to the inlet side of the cell separator 6 described in the item ①, through a tube having between its ends a three-way stopcock 9 having a bag for cell recovery 10 connected thereto, a mesh chamber 8, and a diverging point to a tube with a spike 13 to be connected to a bottle of physiological saline for rinsing. A drain bag 12 was connected to the outlet side of the cell separator 6 through a tube having between its ends a three-way stopcock 11 for connecting a syringe for recovery. The fluid containing nucleated cells in the starting-blood bag 7 was introduced into the cell separator at a fall of about 60 cm, and a fluid containing erythrocytes which had flowed out of the cell separator 6 was discharged into the drain bag 12. Then, the spike 13 was stuck into the bottle of physiological saline, and the clamp 14 was opened, whereby the inside of the filter was rinsed with about 20 ml of physiological saline to rinse away a slight amount of erythrocytes and platelets, which remained in the filter. Subsequently, a 30-ml disposable syringe containing 25 ml of the recovering liquid was connected to the three-way stopcock 11, and the three-way stopcock 11 was turned in such a direction that the syringe communicated only with the cell separator. The three-way stopcock 9 was turned in such a direction that the cell separator 6 communicated only with the bag for cell recovery 10. Then, the piston of the syringe was pushed to recover cells captured in the cell separator, into the bag for cell recovery 10.

④ Analysis

The number of nucleated cells, the number of mononuclear cells, the number of erythrocytes and the number of platelets were determined with an automatic hemocytometer. The percentage of CD34-positive cells based on the total number of nucleated cells was measured by the use of FITC-labeled anti-CD34 antibody according to a flow cytometry method comprising development on SSC-FITC (Miyazaki et al. "Nichijo Shinryo to Ketsueki (Routine Diagnosis and Treatment, and Blood)" Vol. 5, No. 2, pp. 21–24, 1995).

The recovery and the removal rate are calculated by the following equations:

Recovery (%)=100×(number of recovered cells/number of cells in starting cell population)

Removal rate (%)=100−100×(number of recovered cells/number of cells in starting cell population)

⑤ Results

The time required for pushing the piston of the syringe completely was 3 seconds. The linear speed was calculated to be 55.6 cm/min. The results are summarized in Table 6. It can be seen that nucleated cells, mononuclear cells and CD34-positive cells could be recovered at high percentages in the cell suspension recovered, and that erythrocytes and platelets were removed at high percentages.

TABLE 6

| Recovery (%) | | | Removal rate (%) | |
|---|---|---|---|---|
| Nucleated cell | Mono-nuclear cell | CD34-positive cell | Erythrocyte | Platelet |
| 74.3 | 91.2 | 97.6 | 99.0 | 88.0 |

INDUSTRIAL APPLICABILITY

As described above, according to the present invention, useful cells such as hematopoietic stem cells can be recovered with high recovery by a simple and rapid procedure, and the thus obtained cell-containing fluid can be subjected to cryopreservation without a subsequent troublesome cell suspension preparation procedure, and hence can be utilized in a laborsaving cell processing in medical-care-related industries such as the field of hematopoietic stem cell transplatation, the field of adoptive-immuno therapy, etc.

What is claimed is:

1. A cell separation method comprising the steps of:
   (a) introducing a cell-containing fluid, containing cells to be recovered and cells to be removed, into a cell-capturing means which substantially captures said cells to be recovered and substantially permits passage therethrough of said cells to be removed, whereby said cell-capturing means comprises one of a porous structure of nonwoven fabric having a fiber diameter of 1.0–30 μm and a porous spongy structure having a pore size of 2.0–25 μm;
   (b) taking out the resulting fluid containing the cells to be removed from said cell-capturing means; and
   (c) introducing a liquid with a viscosity of not more than 100 mPa·s and not less than 5 mPa·s into said cell-capturing means at a linear speed of at least 0.5 cm/min to recover therefrom said cells to be recovered which have been captured by said cell-capturing means.

2. A cell separation method according to claim 1, wherein the cells to be removed are cells having a surface marker different from that of the cells to be recovered.

3. A cell separation method according to claim 1, wherein the cell-containing fluid containing cells to be recovered and cells to be removed is cord blood.

4. A cell separation method according to claim 1, wherein the cell-containing fluid containing cells to be recovered and cells to be removed is bone marrow.

5. A cell separation method according to claim 1, wherein the cell-containing fluid containing cells to be recovered and cells to be removed is peripheral blood.

6. A cell separation method according to claim 1, wherein the cell-capturing means is obtained by packing said porous structure into a container having a liquid inlet and a liquid outlet.

7. A cell separation method according to claim 1, wherein the cell-capturing means comprises a cell separator having an antibody immobilized therein which reacts to an antigen present in the cells to be recovered, but not in the cells to be removed.

8. A method according to claim 1, wherein the liquid with a viscosity of not more than 500 mPa·s and not less than 5 mPa·s is one which can be used as a preservative for the cells to be recovered.

9. A method according to claim 1, wherein the liquid with a viscosity of not more than 500 mPa·s and not less than 5 mPa·s is a solution containing dextran.

10. A method according to claim 1, which further comprises a step of introducing a liquid with a viscosity of less than 5 mPa·s into the cell-capturing means before the introduction of the liquid with a viscosity of not more than 500 mPa·s and not less than 5 mPa·s.

11. A cell separation method according to claim 1, wherein after recovering the cells to be recovered by introducing a liquid with a viscosity of not more than 500 mPa·s and not less than 5 mPa·s, another liquid is further introduced into the cell-capturing means to collect remaining cells or cell constituents in said cell-capturing means.

12. A method according to claim 1, wherein the direction of introduction of the liquid with a viscosity of not more than 500 mPa·s and not less than 5 mPa·s is opposite to the direction of introduction of the cell-containing fluid containing cells to be recovered and cells to be removed.

13. A cell separation method according to claim 1, wherein the cells to be recovered are nucleated cells.

14. A cell separation method according to claim 13, wherein the nucleated cells are a mononuclear cell fraction containing hematopoietic stem cells.

15. A cell separation method according to claim 13, wherein the nucleated cells are hematopoietic stem cells.

16. A cell separation method according to claim 1, wherein the cells to be removed are cells having no nucleus.

17. A cell separation method according to claim 16, wherein the cells having no nucleus are at least one of erythrocytes and platelets.

18. A cell separation method comprising the steps of:
   (a) introducing a cell-containing fluid, containing cells to be recovered and cells to be removed, into a cell-capturing means which substantially captures said cells to be recovered and substantially permits passage therethrough of said cells to be removed, whereby said cell-capturing means comprises one of a porous structure of nonwoven fabric having a fiber diameter of 1.0–30 μm and a porous spongy structure having a pore size of 2.0–25 μm;
   (b) introducing said cell-containing fluid through a line connected upstream to an inlet of said cell-capturing means;
   (c) taking out the resulting fluid containing said cells to be removed through an outlet of said cell-capturing means;

(d) introducing a liquid with a viscosity of not more than 100 mPa·s and not less than 5 mPa·s into said cell-capturing means through a line connected downstream to the outlet of said cell-capturing means at a linear speed of at least 0.5 cm/min; and (e) recovering said cells to be recovered which have been captured by said cell-capturing means through a line connected upstream to the inlet of said cell-capturing means.

19. A cell separation method according to claim 18, which comprises the steps of recovering the cells through the line connected upstream to the inlet of the cell-capturing means, and then sealing up and separating said line.

20. A cell separation and preservation method comprising the steps of:

(a) introducing a cell-containing fluid, containing cells to be recovered and cells to be removed, into a cell-capturing means which substantially captures said cells to be recovered and substantially permits passage therethrough of said cells to be removed, whereby said cell-capturing means comprises a porous structure of nonwoven fabric having a fiber diameter of 1.0–30 µm and a porous spongy structure having a pore size of 2.0–25 µm;

(b) taking out the resulting fluid containing the cells to be removed from said cell-capturing means;

(c) introducing a liquid with a viscosity of not more than 100 mPa·s and not less than 5 mPa·s into said cell-capturing means at a linear speed of at least 0.5 cm/min to recover therefrom said cells to be recovered which have been captured by said cell-capturing means; and (d) preserving said recovered cells.

21. A cell separation and preservation method according to claim 20, wherein the preservation is cryopreservation.

22. A cell separation system comprising a cell-capturing means which is capable of substantially capturing cells to be recovered and substantially permitting passage therethrough of cells to be removed, wherein said cell-capturing means comprises one of a porous structure of nonwoven fabric having a fiber diameter of 1.0–30 µm and a porous spongy structure having a pore size of 2.0–25 µm, and having at least an inlet and an outlet; a line for introducing into the cell-capturing means a cell-containing fluid containing the cells to be recovered and the cells to be removed which is connected upstream to the inlet of said cell-capturing means; a line for introducing a liquid into said cell-capturing means which is connected down-stream to the outlet of said cell-capturing means; and a line for cell recovery from the inlet side of said cell-capturing means, which is connected upstream to the inlet of said cell-capturing means.

23. A cell separation system according to claim 22, which further comprises a line for introducing a liquid into said cell-capturing means, which is connected up-stream to the inlet of the cell-capturing means or down-stream to the outlet of the cell-capturing means.

24. A cell separation system according to claim 22, wherein the line for cell recovery on the inlet side of said cell-capturing means which is connected upstream to the inlet of the cell-capturing means, is one which has a flow path changing means and a plurality of branches.

25. A cell separation system according to claim 22, wherein the line for cell recovery from the inlet side of said cell-capturing means which is connected upstream to the inlet of the cell-capturing means is made of a material able to withstand freezing and thawing.

26. A cell separation system according to claim 25, wherein the line for cell recovery is one which comprises a freeze bag.

* * * * *